(12) United States Patent
Marcus

(10) Patent No.: US 8,377,419 B2
(45) Date of Patent: Feb. 19, 2013

(54) HYPERPOLARIZED SOLID MATERIALS WITH LONG SPIN RELAXATION TIMES FOR USE AS IMAGING AGENTS IN MAGNETIC RESONANCE IMAGING

(75) Inventor: Charles M. Marcus, Winchester, MA (US)

(73) Assignee: The President and Fellows of Harvard College, Cambridge, MA (US)

( * ) Notice: Subject to any disclaimer, the term of this patent is extended or adjusted under 35 U.S.C. 154(b) by 710 days.

(21) Appl. No.: 12/088,357

(22) PCT Filed: Sep. 28, 2006

(86) PCT No.: PCT/US2006/037725
§ 371 (c)(1),
(2), (4) Date: Oct. 9, 2008

(87) PCT Pub. No.: WO2007/038626
PCT Pub. Date: Apr. 5, 2007

(65) Prior Publication Data
US 2009/0214433 A1 Aug. 27, 2009

Related U.S. Application Data

(60) Provisional application No. 60/721,292, filed on Sep. 28, 2005.

(51) Int. Cl.
*A61B 5/055* (2006.01)
(52) U.S. Cl. ....... 424/9.3; 424/1.11; 424/1.65; 424/1.81
(58) Field of Classification Search ................. 424/1.11, 424/1.65, 1.81, 1.85, 1.89, 9.1, 9.2, 9.3, 9.32, 424/9.321, 9.322, 9.323, 9.34, 9.341, 9.35, 424/9.351, 9.36, 9.361, 9.362, 9.363, 9.364, 424/9.365, 9.37
See application file for complete search history.

(56) References Cited

U.S. PATENT DOCUMENTS

| | | | |
|---|---|---|---|
| 5,144,238 A | 9/1992 | Ehnholm et al. | |
| 5,314,679 A | 5/1994 | Lewis et al. | |
| 5,322,065 A | 6/1994 | Leunbach | |
| 5,515,863 A | 5/1996 | Damadian | |
| 5,525,556 A | 6/1996 | Dunmead et al. | |
| 5,545,396 A | 8/1996 | Albert et al. | |
| 5,641,434 A | 6/1997 | Yamada et al. | |
| 5,662,279 A | 9/1997 | Czekai et al. | |
| 5,827,501 A | 10/1998 | Jorgensen et al. | |
| 5,903,149 A | 5/1999 | Gonen et al. | |
| 6,011,396 A | 1/2000 | Eckels et al. | |
| 6,042,809 A | 3/2000 | Tournier et al. | |
| 6,123,919 A | 9/2000 | Albert et al. | |
| 6,251,522 B1 | 6/2001 | Tanaka et al. | |
| 6,278,893 B1 | 8/2001 | Ardenkjaer-Larsen et al. | |
| 6,311,086 B1 | 10/2001 | Ardenkjaer-Larsen et al. | |
| 6,426,058 B1 * | 7/2002 | Pines et al. ..................... | 424/9.3 |
| 6,453,188 B1 | 9/2002 | Ardenkjaer-Larsen et al. | |
| 6,466,814 B1 | 10/2002 | Ardenkjaer-Larsen et al. | |
| 6,488,910 B2 | 12/2002 | Driehuys | |
| 6,574,495 B1 | 6/2003 | Golman et al. | |
| 6,574,496 B1 | 6/2003 | Golman et al. | |
| 6,593,144 B2 | 7/2003 | Albert et al. | |
| 6,818,202 B2 | 11/2004 | Pines et al. | |
| 6,924,150 B1 | 8/2005 | Xiang et al. | |
| 2001/0000726 A1 | 5/2001 | Albert et al. | |
| 2002/0043267 A1 | 4/2002 | Weiler et al. | |
| 2002/0058869 A1 | 5/2002 | Axelsson et al. | |
| 2002/0146371 A1 | 10/2002 | Li et al. | |
| 2003/0009126 A1 | 1/2003 | Zollinger et al. | |
| 2003/0103890 A1 | 6/2003 | Konya et al. | |
| 2003/0185760 A1 | 10/2003 | Lanza et al. | |
| 2003/0212323 A1 | 11/2003 | Petersson et al. | |
| 2004/0001841 A1 | 1/2004 | Nagavarapu et al. | |
| 2004/0015075 A1 | 1/2004 | Kimchy et al. | |
| 2004/0023855 A1 | 2/2004 | John et al. | |
| 2004/0024307 A1 | 2/2004 | Golman et al. | |
| 2004/0170820 A1 | 9/2004 | Yadav et al. | |
| 2004/0171928 A1 | 9/2004 | Petersson et al. | |
| 2005/0030026 A1 | 2/2005 | Pines et al. | |
| 2005/0136002 A1 | 6/2005 | Fossheim et al. | |
| 2005/0197677 A1 | 9/2005 | Stevenson | |
| 2005/0238391 A1 | 10/2005 | Hibino | |
| 2005/0266697 A1 | 12/2005 | Korgel et al. | |
| 2006/0206270 A1 | 9/2006 | Raftery et al. | |
| 2007/0116602 A1 | 5/2007 | Lee | |

FOREIGN PATENT DOCUMENTS

| | | |
|---|---|---|
| DE | 102005017927 A1 | 10/2006 |
| WO | WO 9000904 | 2/1990 |
| WO | WO 9858272 | 12/1998 |
| WO | WO 9924080 | 5/1999 |
| WO | WO 0117567 | 3/2001 |
| WO | WO-0223209 A2 | 3/2002 |
| WO | WO-03023432 A1 | 3/2003 |
| WO | WO-2005/069027 A1 | 7/2005 |
| WO | WO-2006111126 A2 | 10/2006 |

(Continued)

OTHER PUBLICATIONS

Seydoux et al (J. Phys. Chem. B, 1999, vol. 103, pp. 4629-4637).*

(Continued)

*Primary Examiner* — D L Jones
(74) *Attorney, Agent, or Firm* — Choate, Hall & Stewart LLP; Charles E. Lyon; Jeffrey Pelligrino

(57) ABSTRACT

An imaging agent is disclosed for use in nuclear magnetic resonance imaging. The imaging agent includes a first substance and a second substance. The first substance includes at least one atom having non-zero nuclear spin providing a polarized magnetic orientation. The second substance is bound to the first substance and inhibits physical contact between the at least one atom and other atoms and molecules to thereby inhibit spin relaxation of the polarized magnetic orientation of the at least one atom.

13 Claims, 2 Drawing Sheets

FOREIGN PATENT DOCUMENTS

| | | | |
|---|---|---|---|
| WO | WO-2007/038626 A2 | 4/2007 | |
| WO | WO-2007/070466 A2 | 6/2007 | |

OTHER PUBLICATIONS

Ardenkjaer-Larsen J. H. et al. National Academy of Science, Washington, D.C. US, 10158-10163: vol. 100. No. 18.
European Search Report for 06847555.7 dated Oct. 2, 2009.
European Search Report for 07709721.0 dated Oct. 2, 2009.
Rogers, W. et al. Nature Clinical Practice Cardiovascular Medicine 3:10: 554-562:2006.
Shulman and Wyluda, Phys. Rev. 103:1127, 1956.
Subramanian et al., NMR Biomed. 17:263, 2004.
Tallheden, T., et al., Life Sciences 79: 999-1006: 2006.
Aime, et al., *Journal of Chemical Physics*, 119(17):8890-8896 (2003).
Charles Marcus, "BioBeacon—Market Pain: identify effective cancer treatments, save lives & money with functional MRI imaging", presented on Apr. 26, 2007 by Jacob Aptekar as part of a business school course taught by Lee Fleming.
Golman et al., PNAS 100(18):10435-10439 (2003).
Golman et al., *The British Journal of Radiology*, 76:S118-S127 (2003).
International Search Report and Written Opinion of International Searching Authority, PCT/US06/37725, mailed on Mar. 13, 2007.
International Search Report and Written Opinion of International Searching Authority, PCT/US06/47205, mailed on Jan. 11, 2008.
International Search Report and Written Opinion of International Searching Authority, PCT/US07/00788, mailed on Sep. 28, 2007.
Johnson, et al., "Hyperpolarized Nanoparticles for Magnetic Resonance Imgaing", presented in May 2006 at a Harvard Symposium.
Tiefenauer et al., *Bioconjugate Chem.* 4:347-352 (1993).
Ager et al. (2005) "High-Purity, Isotopically Enriched Bulk Silicon," J. Electrochem. Soc., 152(6):G488-G451.
Ahmed et al. (2001) "Bioadhesive Microdevices for Drug Delivery: A Feasibility Study," Biomed. Microdevices, 3(2):89-96.
Aime et al. (2003) "Hyperpolarization transfer from parahydrogen to deuterium via carbon-13" J. Chem. Phys., 119(17):8890-8896.
Akerma et al. (2002) "Nanocrystal targeting in vivo," PNAS, 99(20):12617-12621.
Arap et al. (1998) "Cancer treatment by targeted drug delivery to tumor vasculature in a mouse model," Science, 279:377-380.
Bhushan et al. (2005) "Morphology and adhesion of biomolecules on silicon based surfaces," Acta Biomater., 1:327-341.
Capaccio et al. (2005) "Coupling Biomolecules to Fullerenes through a Molecular Adapter," Bioconjugate Chem., 16(2):241-244.
Cotten et al. (1993) "Receptor-Mediated Transport of DNA into Eukaryotic Cells," Methods Enzymology, 217:618-644.
Fatouros et al. (2006) "In Vitro and in Vivo Imaging Studies of a New Endohedral Metallofullerene Nanoparticle," Radiology, 240(3):756-764.
Garnett (2001) "Targeted drug conjugates: principles and progress," Advanced Drug Delivery Reviews, 53:171-216.
Golman et al. (2003) "Molecular imaging using hyperpolarized 13C," The British Journal of Radiology, 76:S118-S127.
Golman et al. (2003) "Molecular imaging with endogenous substances," PNAS, 100(18):10435-10439.
Graebner et al. (1994) "Improved thermal conductivity in isotopically enriched chemical vapor deposited diamond," Appl. Phys. Lett., 64(19):2549-2551.
Gref et al. (1994) "Biodegradable long-circulating polymeric nanospheres," Science, 263:1600-1603.
Haller (1995) "Isotopically engineered semiconductors," J. Appl. Phys., 77(7):2857-2878.
International Search Report for PCT/US06/37725 (date of mailing Mar. 13, 2007).
International Search Report for PCT/US06/47205 (date of mailing Jan. 11, 2008).
International Search Report for PCT/US07/00788 (date of mailing Sep. 28, 2007).
International Search Report for PCT/US09/30672 (date of mailing Mar. 11, 2009).
Johnson et al. (2006) "Hyperpolarized Nanoparticles for Magnetic Resonance Imaging," Harvard University Center for Nanoscale Systems, presented at a Harvard Symposium (1 page).
Katz et al. (2004) "Biomolecule-Functionalized Carbon Nanotubes: Applications in Nanobioelectronics," ChemPhysChem, 5:1084-1104.
Kumar et al. (2007) "PEGylated Dendritic Architecture for Development of a Prolonged Drug Delivery System for an Antitubercular Drug," Current Drug Delivery, 4(1):11-19.
Li et al. (2005) "Functionalization of single-walled carbon nanotubes with well-defined polystyrene by 'click' coupling," J. Am. Chem. Soc., 127:14518-14524.
Marcus (2007) "BioBeacon—Market Pain: identify effective cancer treatments, save lives & money with functional MRI imaging," Harvard Department of Physics, Director of harved Center for Nanoscale Systems (CNS), presented by Jacob as part of Business School course taught by Lee Fleming on Apr. 26, 2007.
Montet et al. (2006) "Multivalent effects of RGD peptides obtained by nanoparticle display," J. Med. Chem., 49:6087-6093.
Nakamura et al. (2003) "Functionalized Fullerenes in Water. The First 10 Years of Their Chemistry, Biology, and Nanoscience," Acc. Chem. Res., 36(11):807-815.
Pantarotto et al. (2004) "Synthesis and Biological Properties of Fullerene-Containing Amino Acids and Peptides," Mini-Rev. Med. Chem., 4:805-814.
Shirahata et al. (2005) "Monolayer-Derivative Functionalization of Non-oxidized Silicon Surfaces," Chem. Rec., 5:145-159.
Simberg et al. (2007) "Biomimetic amplification of nanoparticle homing to tumors," PNAS, 104(3):932-936.
Supplementary European Search Report for EP 06 81 5599.3 (date of completion Mar. 31, 2010).
Tiefenauer et al. (1993) "Antibody-Magnetite Nanoparticles: in Vitro Characterization of a Potential Tumor-Specific Contrast Agent for Magnetic Resonance Imaging," Bioconjugate Chem., 4:347-352.
Vliet et al. (1999) "Discovery of the Near-Infrared Window into the Body and the Early Development of Near-Infrared Spectroscopy," J. Biomed. Opt., 4(4):392-396.
Written Opinion for PCT/US06/37725 (date of mailing Mar. 13, 2007).
Written Opinion for PCT/US06/47205 (date of mailing Jan. 11, 2008).
Written Opinion for PCT/US07/00788 (date of mailing Sep. 28, 2007).
Written Opinion for PCT/US09/30672 (date of mailing Mar. 11, 2009).
Bagraev et al., "Spectral distribution of polarization of nuclei in impurity absorption of light in silicon," JETP Lett., 28(8): 488-490, 1978.
Bregman, A., "Differential Centrifugation," Biology 212: Cell Biology, pp. 1-4, 2003.
Dementyev et al., "Dynamic Nuclear Polarization in Silicon Microparticles," Physical Review Letters 100, pp. 127601-1-127601-4, 2008.
Mikawa et al., "Paramagnetic Water-Soluble Metallofullerenes Having the Highest Relaxivity for MRI Contrast Agents," Bioconjugate Chem., 12: 510-514, 2001.
Verhultst, A., "Optical Pumping Experiments to Increase the Polarization in Nuclear-Spin Based Quantum Computers," PhD Thesis, Stanford University, pp. i-xxxiv and 1-251, 2004.

\* cited by examiner

HYPERPOLARIZED SOLID MATERIALS WITH LONG SPIN RELAXATION TIMES FOR USE AS IMAGING AGENTS IN MAGNETIC RESONANCE IMAGING

PRIORITY

The present application claims priority under 35 U.S.C. §371 to International Application No. PCT/US2006/037725, filed Sep. 28, 2006,which claims priority to U.S. Provisional Application No. 60/721,292, filed Sep. 28, 2005. The entire contents of each of the above-referenced applications are incorporated herein by reference.

BACKGROUND

The invention generally relates to the field of nuclear magnetic resonance (NMR), and relates in particular to magnetic resonance imaging (MRI).

MRI systems generally provide for diagnostic imaging of regions within a subject by detecting the precession of the magnetic moments of atomic nuclei in an applied external magnetic field. Spatial selectivity, allowing imaging, is achieved by matching the frequency of an applied radio-frequency (rf) oscillating field to the precession frequency of the nuclei in a quasi-static field. By introducing controlled gradients in the quasi-static applied field, specific slices of the subject can be selectively brought into resonance. By a variety of methods of controlling these gradients in multiple directions, as well as controlling the pulsed application of the rf resonant fields, three-dimensional images representing various properties of the nuclear precession can be detected, giving information about the density of nuclei, their environment, and their relaxation processes. By appropriate choice of the magnitude of the applied quasi-static field and the rf frequency, different nuclei can be imaged. Typically, in medical applications of MRI, it is the nuclei of hydrogen atoms, i.e., protons, that are imaged. This is, of course, not the only possibility. Information about the environment surrounding the nuclei of interest can be obtained by monitoring the relaxation process whereby the precessional motion of the nuclei is damped, either by the relaxation of the nuclear moment orientation returning to alignment with the quasi-static field following a tipping pulse (on a time scale T1), or by the dephasing of the precession due to environmental effects that cause more or less rapid precession, relative to the applied rf frequency (on a time scale T2).

Conventional MRI contrast agents, such as those based on gadolinium compounds, operate by locally altering the T1 or T2 relaxation processes of protons. Typically, this relies on the magnetic properties of the contrast agent, which alters the local magnetic environment of protons. In this case, when images display either of these relaxation times as a function of position in the subject, the location of the contrast agent shows up in the image, providing diagnostic information.

An alternative approach to MRI imaging is to introduce into the subject an imaging agent, the nuclei of which themselves are imaged by the techniques described above. That is, rather than affecting the local environment of the protons in the body and thereby providing contrast in a proton image, the imaging agent is itself imaged. Such imaging agents include substances that have non-zero nuclear spin such as $^3$He, $^{129}$Xe, $^{31}$P, $^{29}$Si, $^{13}$C and others. The nuclei in these substances may be polarized by various methods (including optically or using sizable applied magnetic fields at room or low temperature), orienting a significant fraction of the nuclei in the agent (hyperpolarizing), before introduction into the body, and then introducing the polarized material into the body. Once in the body, a strong imaging signal is obtained due to the high degree of polarization of the imaging agent. Also there is only a small background signal from the body, as the imaging agent has a resonant frequency that does not excite protons in the body. For example, U.S. Pat. No. 5,545,396 discloses the use of hyperpolarized noble gases for MRI.

Many proposed agents for hyperpolarized MRI have short relaxation (T1) times, requiring that the material be quickly transferred from the hyperpolarizing apparatus to the body, and imaged very soon after introduction into the body, often on the time scale of tens of seconds. For a number of applications, it is desirable to use an imaging agent with longer T1 times. For example, U.S. Pat. No. 6,453,188 discloses a method of providing magnetic resonance imaging using a hyperpolarized gas that provides a T1 time of several minutes and possibly up to sixteen minutes (1000s). Compared to gases, solid—or liquid materials usually lose their hyperpolarization rapidly. Hyperpolarized substances are, therefore, typically used as gases. Protecting even the hyperpolarized gas from losing its magnetic orientation, however, is also difficult in certain applications. For example, U.S. Published Patent Application No. 2003/0009126 discloses the use of a specialized container for collecting and transporting $^3$He and $^{129}$Xe gas while minimizing contact induced spin relaxation. U.S. Pat. No. 6,488,910 discloses providing $^{129}$Xe gas or $^3$He gas in microbubbles that are then introduced into the body. The gas is provided in the microbubbles for the purpose of increasing the T1 time of the gas. The relaxation time of such gas, however, is still limited.

U.S. Published Patent Application No. 2004/0024307 discloses the use of para-hydrogen labeled imaging agents using non-zero nuclear spin atoms such as $^{13}$C, $^{15}$N, $^{29}$Si, $^{19}$F, $^3$Li, $^1$H, and $^{31}$P in a host molecule using enriched hydrogen. The hydrogenated imaging agent is then employed in a soluble form in a liquid or solvent for MRI and is disclosed to have a T1 time of preferably about 1000 s or longer.

U.S. Published Patent Application No. 2005/0136002 discloses the use of a particulate contrast agent that includes non-zero nuclear spin atoms such as $^{19}$F, $^{13}$C, $^{15}$N, $^{29}$Si, $^{31}$P, $^{129}$Xe and $^3$He. The particulate composition is disclosed to respond to physiological conditions in a subject to provide improved imaging by changing contrast characteristics. The responses to physiological conditions are disclosed to include melting, or changing the viscosity or chemical composition of the subject. The spin relaxation times, however, are generally disclosed to be less than 1 s.

There is a need, therefore, for a contrast agent or imaging agent that provides greater flexibility in designing relaxation times during nuclear magnetic resonance imaging.

SUMMARY OF THE INVENTION

An imaging agent is provided in accordance with an embodiment of the invention for use in nuclear magnetic resonance imaging that includes a first substance and a second substance. The first substance includes at least one atom having non-zero nuclear spin. The second substance is bound to the first substance and provides shielding for the first substance from the environment in a way that allows long nuclear spin relaxation of the first substance, allowing the at least one atom of the first substance to be hyperpolarized with a long relaxation time.

In accordance with various embodiments, the first substance includes at least one of $^{29}$Si, $^{13}$C, $^{19}$F, $^{31}$P, $^{129}$Xe or $^3$He, and the imaging agent may be provided in solid form as a powder.

BRIEF DESCRIPTION OF THE DRAWINGS

The following description may be further understood with reference to the accompanying drawings in which.

The drawings are shown for illustrative purposes and are not to scale.

DETAILED DESCRIPTION OF THE INVENTION

Applicant has discovered, that although liquids and solids typically have short relaxation times, certain solid materials can be manufactured that result in extremely long T1 times, and that these materials can make excellent hyperpolarized contrast agents. Applicant has discovered that a long T1 contrast agent for hyperpolarized MRI application may be formed using a material whose host substance has no nuclear spin and include with it an impurity or dopant that has a nonzero nuclear spin. For example, naturally occurring Si or C, are composed mostly of $^{28}$Si and $^{12}$C respectively, which ate zero nuclear atoms, but also contain $^{29}$Si and $^{13}$C, respectively, which have nuclear spin ½. The concentration of the nonzero-spin component in the zero-nuclear-spin host can be controlled by various methods to range from a few percent, up to 80-90%. The nonzero spin substance can also be a dopant material in the host, such as $^{31}$P in Si. In another embodiment, either natural or artificial concentrations of $^{13}$C in a $^{12}$C constitute such a system. Other embodiments include $^{29}$Si in silica or quartz.

Relaxation times (T1) of the nonzero nuclear component in these solid materials are found to extended considerably beyond other hyperpolarized imaging agents, including gases, with T1 times of at least 30 minutes to an hour and even four hours or beyond at room temperature. The solid may be provided as a powder or, the powder can be suspended in a liquid. Powder sizes ranging from nanoparticles, a few nanometers in diameter, to micron diameters and beyond are possible. These materials appear to be biocompatible, although the powder size should be considered carefully for compatibility with biological systems.

Figure 1:
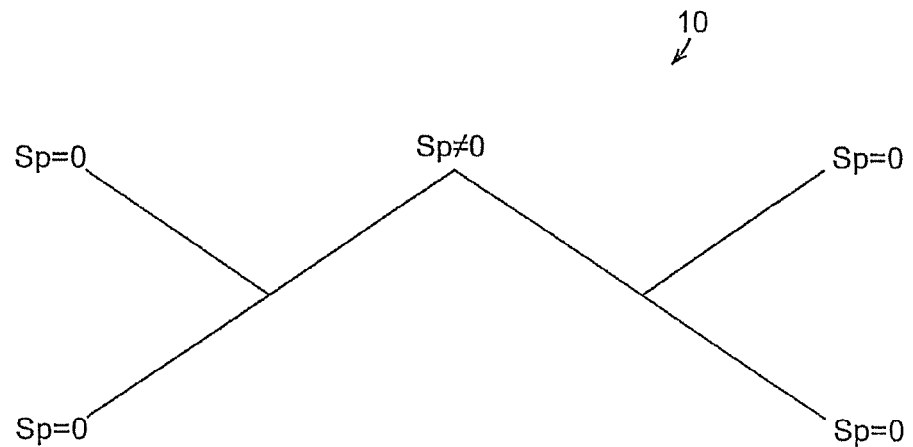
FIG. 1 shows an illustrative diagrammatic view of a molecule of an imaging agent in accordance with an embodiment of the invention.
Figure 2:
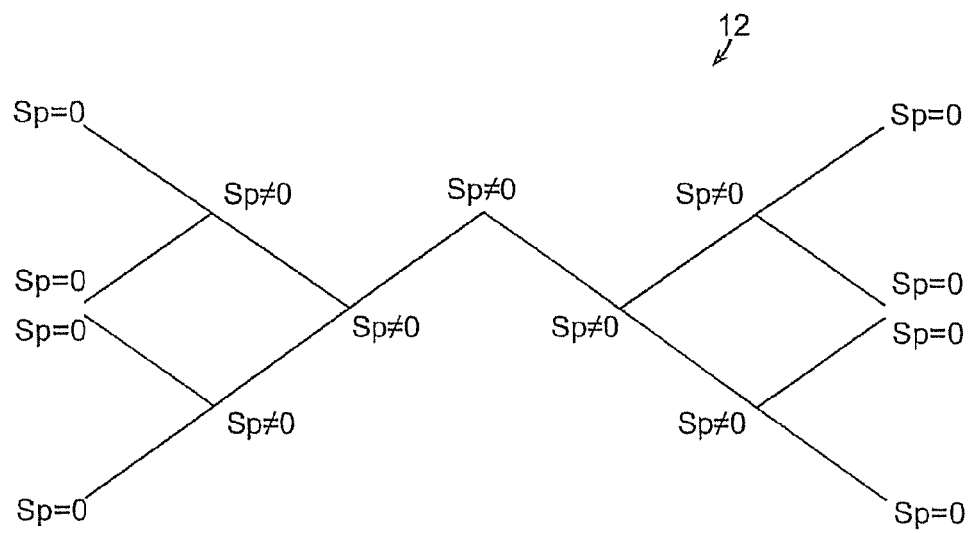
FIG. 2 shows an illustrative diagrammatic view of a molecule of an imaging agent in accordance with another embodiment of the invention.
Figure 3:
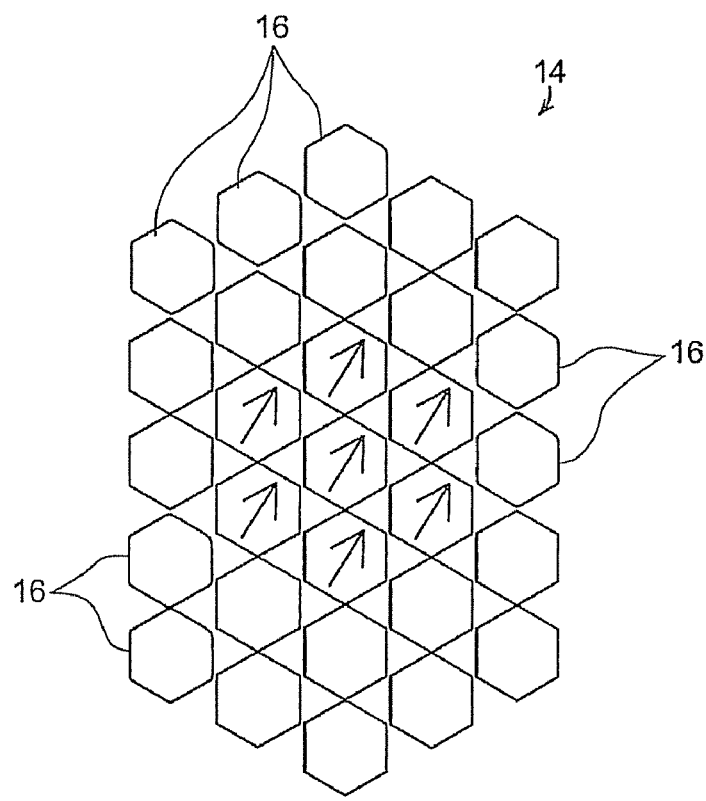
FIG. 3 shows an illustrative diagrammatic view of a particle of an imaging agent in accordance with another embodiment of the invention.
Figure 4:
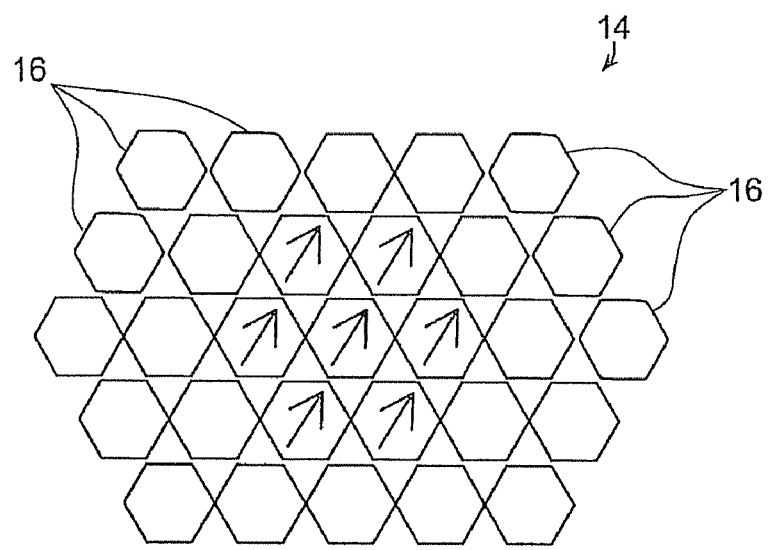
FIG. 4 shows an illustrative diagrammatic view of the particle shown in FIG. 3 rotated 90 degrees.

As shown at 10 in FIG. 1, a molecule may include central atom of a non-zero spin substance such as $^{29}$Si, $^{13}$c, $^{31}$P, $^{129}$Xe or $^{3}$He that is surrounded by atoms of zero-spin substances such as $^{28}$Si or $^{12}$C, or compounds such as $^{28}$SiO$_2$. As shown at 12 in FIG. 2, a molecule in accordance with another embodiment of the invention may include a non-zero spin substance that is surrounded by a zero spin substance. A molecule 14 including zero spin atoms 16 and non-zero spin atoms 18 as shown in FIG. 3. When the molecule 14 is rotated (e.g., 90 degrees) the magnetic orientations of the non-zero spin atoms 18 continue to be oriented in the same direction as shown in FIG. 4.

For particular crystal structures, such as those found naturally occurring in Si or C (diamond) the electronic environment of the nonzero spin component is isotropic, so that weak coupling of electrons to nuclei does not have any preferred orientation. This means that the direction of the nuclear magnetic moment of the nonzero spin component is not locked to the crystal axes of the material, or the particle of material. As a result, even when the individual particles tumble, the nuclear magnetic moment holds its hyperpolarized orientation.

In further embodiments, a binding material may also be included on the surface of the solid imaging agent powder (nanoparticle) to bind to certain biological materials with specificity. As an example, by coating the nanoparticle imaging agent with a substance that preferentially adheres to certain cancer cells, the location of these cells in the body can be imaged by MRI. Nanoparticles of solid material such as silicon, diamond, or silica may be functionalized on the surfaces to cause them to attach to a wide range of specific proteins, cells, or organs, while maintaining long T1 times. This allows specific biological surfaces or processes to be tagged by the hyperpolarized materials.

Various techniques may be used to produce the hyperpolarization of the material prior to introducing it into the biological system or medical patient. These include, but are not limited to, optical dynamical nuclear polarization, various Overhauser techniques (solid effect, thermal effect) and polarization in high magnetic fields and/or low temperatures, including fields produced with permanent magnets.

A wide range of potential applications of hyperpolarized powders with long (up to multi-hour) T1 times include bolus injection into the bloodstream for angiography or examining ruptures in the blood-brain barrier, placement of the hyperpolarized material into body cavities (oral cavity, sinus, gut, esophagus, colon, vagina) allowing, for instance, hyperpolarized virtual colonoscopy and related diagnostics, lung imaging using hyperpolarized inhalants (10-100 nm particles in aerosol).

Those skilled in the art will appreciate that numerous modifications and variations may be made to the above disclosed embodiments without departing from the spirit and scope of the invention.

What is claimed is:

1. A method of detecting a silicon particle within a patient, the method comprising introducing a silicon particle into a patient, wherein the silicon particle comprises a hyperpolarized $^{29}$Si nuclear spin and the size of the silicon particle is between about 10 nm and about 10 μm; and detecting the $^{29}$Si nuclear spin by nuclear magnetic resonance.

2. The method of claim 1, wherein in the step of introducing, the silicon particle is suspended in a liquid.

3. The method of claim 1, wherein the spin relaxation (T1) time of the $^{29}$Si nuclear spin is at least 30 minutes at room temperature.

4. The method of claim 1, wherein the spin relaxation (T1) time of the $^{29}$Si nuclear spin is at least one hour at room temperature.

5. The method of claim 1, wherein the silicon particle includes a binding material on its surface that binds to a biological material.

6. The method of claim 1, wherein the step of detecting comprises imaging the silicon particle by nuclear magnetic resonance imaging.

7. The method of claim 6, wherein the silicon particle is imaged within a bloodstream of the patient.

8. The method of claim 6, wherein the silicon particle is imaged within a body cavity of the patient.

9. The method of claim 6, wherein the silicon particle is imaged within a lung cavity of the patient.

10. The method of claim 1, wherein in the step of introducing, the silicon particle is part of a powder.

11. The method of claim 1, wherein the size of the silicon particle is between about 10 nm and about 100 nm.

12. The method of claim 1, wherein the silicon particle is made of naturally occurring silicon.

13. The method of claim 1, wherein the silicon particle comprises $^{28}SiO_2$.

* * * * *

UNITED STATES PATENT AND TRADEMARK OFFICE
CERTIFICATE OF CORRECTION

PATENT NO.         : 8,377,419 B2                                                    Page 1 of 1
APPLICATION NO. : 12/088357
DATED              : February 19, 2013
INVENTOR(S)        : Charles M. Marcus It is certified that error appears in the above-identified patent and that said Letters Patent is hereby corrected as shown below:

On the Title Page:

The first or sole Notice should read --

Subject to any disclaimer, the term of this patent is extended or adjusted under 35 U.S.C. 154(b) by 998 days.

Signed and Sealed this

First Day of September, 2015

Michelle K. Lee
*Director of the United States Patent and Trademark Office*